United States Patent
Mo et al.

(10) Patent No.: US 7,074,825 B2
(45) Date of Patent: Jul. 11, 2006

(54) COMPOSITION AND METHOD FOR TREATING CANCER

(76) Inventors: Huanbiao Mo, c/o Department of Nutrition and Food Sciences, Texas Woman's University, 304 Administration Dr., Denton, TX (US) 76201; Charles E. Elson, c/o Department of Nutritional Sciences, University of Wisconsin-Madison, 1415 Linden Dr., Madison, WI (US) 53706; Dennis M. Peffley, 1743 NE. Lakeshore Dr., Lee's Summit, MO (US) 64086; Patricia M. Hentosh, 1743 NE. Lakeshore Dr., Lee's Summit, MO (US) 64086

( * ) Notice: Subject to any disclaimer, the term of this patent is extended or adjusted under 35 U.S.C. 154(b) by 201 days.

(21) Appl. No.: 10/383,811

(22) Filed: Mar. 7, 2003

(65) Prior Publication Data

US 2004/0176311 A1    Sep. 9, 2004

Related U.S. Application Data

(60) Provisional application No. 60/362,358, filed on Mar. 7, 2002.

(51) Int. Cl.
*A61K 31/35*    (2006.01)
*A61K 31/335*    (2006.01)

(52) U.S. Cl. .................. 514/456; 514/458; 514/460

(58) Field of Classification Search .............. 514/456, 514/458, 460
See application file for complete search history.

(56) References Cited

U.S. PATENT DOCUMENTS 6,133,312 A * 10/2000 Elson .................. 514/458
6,251,400 B1 * 6/2001 Guthrie et al. ........... 424/736
2004/0110848 A1 * 6/2004 Peffley et al. ............. 514/739

OTHER PUBLICATIONS

Cecil Textbook of Medicine, 21st Edition, vol. 1, published 2000 by W.B. Saunders Company (PA), pp. 1060-1074.*
McAnally, Jennifer A. [M.S.]; Mo, Huanbio [advisor], "Potentiation of the Chemotherapeutic Action of Low-Dose Lovastatin with Genistein and gamma-2-Tocotrienol Demonstrated in Human Prostate and Lung Tumor Cells and Murine Melanoma Cells", Masters Abstract International, (2003) vol. 42, No. 4, p. 1199. Order No. AAI1427573, 50 pages.*
Bravo, Lou [Ph.D.]; Hsueh, Andie [advisor], "The Growth-Suppressive Effects of Farnesol, gamma-Tocotrienol, Genistein, Lovastatin and Pomegranate Extracts Individually and in Combinations on Human Prostate Tumor Cells", Dissertation Abstracts International, (2003), vol. 64, No. 11B, p. 5455, Order No.: AAI3114311. 71 pages.*

Abid Mr, Li Y, et al. (1999)"Translational rregulation of ribonucleotide reductase by eukaryotic initiation factor 4E links protein . . . " J Biol Chem; 274(50): 35991-8.
Agarwal R. (2000)"Cell signaling and regulators of cell cycle as molecular targets for prostate cancer prevention by dietary agents." Biochem Pharmacol;60(8): 1051-9.
Alhasan SA, Aranha O, Sarkar FH. (2001) Genistein elicits pleiotropic molecular effects on head and neck cancer cells. Clin Cancer Res; 7(12): 4174-81.
Asslan R, Pradines A, et al. (1998) "Tyrosine kinase-dependent modulation of 3-hydroxy-3-methylglutaryl-CoA . . . " Biochem J; 330 ( Pt 1): 241-6.
Azrolan NI, Coleman PS. (1989) "A discoordinate increase in the cellular amount of 3-hydroxy-3-methylglutaryl-CoA reductase . . . " Biochem J; 258(2): 421-5.
Brown MS, Goldstein JL. (1997) The SREBP pathway: regulation of cholesterol metabolism by proteolysis of a membrane-bound transcription factor. Cell; 89(3): 331-40.
Chen Y, Hughes-Fulford M. (2001) "Human prostate cancer cells lack feedback regulation of low-density lipoprotein receptor . . . " Int J Cancer; 91(1): 41-5.
Coleman PS, Chen LC, Sepp-Lorenzino L. (1997) Cholesterol metabolism and tumor cell proliferation. Subcell Biochem; 28: 363-435.
Constantinou A, Huberman E. (1995) "Genistein as an inducer of tumor cell differentiation: possible . . . " Proc Soc Exp Biol Med; 208(1): 109-15.
Correll CC, NG L, Edwards PA. (1994) "Identification of farnesol as the non-sterol derivative of mevalonic acid required . . . ". J Biol Chem; 269(26): 17390-3.
Coxon FP, Helfrich MH,et al (2001) "Identification of a novel phosphonocarboxylate inhibitor of Rab geranylgeranyl . . . " J Biol Chem; 276(51): 48213-22.
Elson CE. (1995) "Suppression of mevalonate pathway activities by dietary isoprenoids: protective roles in cancer . . . " J Nutr; 125(6 Suppl): 1666S-1672S.

(Continued)

*Primary Examiner*—Raymond J. Henley, III
(74) *Attorney, Agent, or Firm*—Loren K. Thompson

(57) ABSTRACT

A composition and an associated method of treating cancer cells by impeding cancer cell growth with the composition are disclosed. The composition includes at least a first and a second HMG-CoA reductase inhibitor, wherein the total amount of the first and second HMG-CoA reductase inhibitors is effective in synergistically impeding cancer cell growth and wherein the cancer cell growth synergistic impedance from the total amount of the first and second HMG-CoA reductase inhibitors is greater than a theoretical additive effect from the combined first and second HMG-CoA reductase inhibitors. The present composition does not simultaneously contain both a tocotrienol and an ionone when the composition contains only a first and a second HMG-CoA reductase inhibitor. The method includes treating cancer cells with the claimed composition to impede cancer cell growth.

7 Claims, No Drawings

OTHER PUBLICATIONS

Elson CE, Peffley DM, et al.(1999) "Isoprenoid-mediated inhibition of mevalonate synthesis: potential . . . " Proc Soc Exp Biol Med; 221(4): 294-311.

Engfelt WH, Shackelford JE, et al (1997) "Characterization of UT2 cells. The induction of peroxisomal . . . " J Biol Chem; 272(39): 24579-87.

Engstrom W, Schofield PN. (1987) "Expression of the 3-hydroxy-3-methylglutaryl coenzyme A-reductase alnd LDL-receptor . . . " Anticancer Res;(3 Pt B): 337-42.

Ericsson J, Jackson SM, et al (1996) "Sterol regulatory element binding protein binds to a cis element in the promotor . . . " Proc Natl Acad Sci U S A; 93(2): 945-50.

Ericsson J, Usheva A, Edwards PA. (1999) "YY1 is a negative regulator of transcription of three sterol regulatory . . . " J Biol Chem; 274(20): 14508-13.

Fournier DB, Erdman JW, JR., et al.(1998) "Soy, its components, and cancer prevention: a review . . . " Cancer Epidemiol Blomarkers Prev; 7(11): 1055-65.

Fritz T, Buechler, R. et al (1998) "Translational efficiency of 3-hydroxy-3-methylglutaryl coenzyme A (HMG-CoA) . . . " Circ Res; 98: 379.

Gayen AK, Peffley DM. (1995) "The length of 5'-untranslated leader sequences influences distribution of . . . " Arch Biochem Biophys; 322(2): 475-85.

Gardner RG, Shearer AG, et al (2001) "In vivo action of the HRD ubiquitin ligase complex: mechanisms of endoplasmic . . . " Mol Cell Biol; 21(13): 4276-91.

Goldstein JL, Brown MS. (1990) Regulation of the mevalonate pathway. Nature: 343(6257): 425-30.

Guan G, Jiang G, et al. (1995) Molecular cloning and functional analysis of the promoter of the human squalene synthase gene. J Biol Chem; 270(37): 21958-65.

Hentosh P, Yuh SH, et al. (2001) Sterol-independent regulation of 3-hydroxy-3-methylglutaryl coenzyme A reductase in tumor cells. Mol Carcinog; 32(3): 154-66.

Hotz MA, Gong J. Traganos F, Darzynkiewicz Z. (1994) "Flow cytometric detectioin of apoptosis: comparison . . . " Cytometry; 15(3): 237-44.

Jackson RJ, Wickens M. (1997) Translational controls impinging on the 5'-untranslated region and initiation factor proteins. Curr Opin Genet Dev; 7(2): 233-41.

Jiang Y, Muschel RJ. (2002) Regulation of matrix metalloproteinase-9 (MMP-9) by translational efficiency in murine prostate carcinoma cells. Cancer Res; 62(6): 1910-4.

Jirtle RL, Haag JD, et al. (1993) "Increased mannose 6-phosphate/insulin-like growth factor II receptor and transforming growth factor beta . . . " Cancer Res; 53(17): 3849-52.

Jones RM, Branda J,et al (1996) "An essential E box in the promoter of the gene encoding the mRNA cap-binding protein . . . " Mol Cell Biol; 16(9): 4754-64.

Kelloff GJ, Fay Jr, et al. (1996) "Epidermal growth factor receptor kinase inhibitors as potential . . . " Cancer Epidemiol Biomarkers Prev; 5(8): 657-66.

Kevil CG, DE Benedetti A, et al. (1996) "Translational regulation of vascular permeability factor by eukaryotic initiation factor 4E: . . . " Int J Cancer; 65(6): 785-90.

Knight JB, Cao KT, et al. (2000) "Expression of a prenylation-deficient Rab4 interferes with propagation of insulin signaling through . . . " Endocrinology; 141(1): 208-18.

Kotzka J, Muller-Wieland D, et al. (2000) "Sterol regulatory element binding proteins (SREBP)-1a and SREBP-2 are linked to the MAP-kinase cascade." J Lipid Res; 41(1): 99-108.

Levitzki A, Gazit A. (1995) Tyrosine kinase inhibition: an approach to drug development. Science; 267(5205): 1782-8.

LI BD, Liu L, Dawson M OE Benedetti A. (1997) Overexpression of eukaryotic initiation factor 4E (eIF4E) in breast carcinoma. Cancer; 79(12): 2385-90.

LI S, Sonenberg N, et al. (2002) "Translational control of cell fate: availability of phosphorylation sites on translational . . . " Mol Cell Biol; 22(8): 2853-61.

Liu JF, Crepin M, Liu JM. et al. (2002) "FGF-2 and TPA induce matrix metalloproteinase-9 secretion in MCF-7 cells through . . . " Biochem Biophys Res Commun; 296(4): 1174-82.

Lopez JM, Bennett MK, et al (1996) "Sterol regulation of acetyl coenzyme A carboxylase: a mechanism for coordinate control . . . " Proc Natl Acad SCi U S A; 93(3): 1049-53.

Magana MM, Osborne TF. (1996) "Two landem binding sites for sterol regulatory element binding proteins are required for sterol . . . " J Biol Chem; 271(51): 32689-94.

Makela SI, Pylkkanen LH, Santti RS, Adlercreutz H. (1995) Dietary soybean may be antiestrogenic in male mice. J Nutr. 125(3): 437-45.

Matsukawa Y, Marui N, Sakai T, et al. (1993) Genistein arrests cell cycle progression at G2-M. Cancer Res; 53(6): 1328-31.

Mills JJ, Chari RS, Boyer IJ, Gould MN, Jirtle RL. (1995) Induction of apoptosis in liver tumors by the monoterpene perillyl alcohol. Cancer Res; 55(5): 979-83.

Miyagi Y, Sugiyama A, et al. (1995) "Elevated levels of eukaryotic translation initiation factor eIF-4E, mRNA in a broad spectrum . . . " Cancer Lett; 91(2): 247-52.

Moriyama T, Wada M, et al (2001) "3-hydroxy-3-methylglutaryl coenzyme A reductase is sterol-dependently cleaved by cathepsin L-type . . . " Arch Biochem Biophys; 386(2): 205-12.

Moses MA, Wiederschain D, et al. (1998) Increased incidence of matrix metalloproteinases in urine of cancer patients. Cancer Res; 58(7): 1395-9.

Overmeyer JH, Malese WA. (1992) Isoprenoid rerquirement for intracellular transport and processing of murine leukemia virus envelope protein. J Biol Chem; 267(31): 22686-92.

Pagliacci MC, Smacchia M, et al. (1994) Growrth-inhibitory effects of the natural phyto-oestrogen genistein in MCF-7 human breast cancer cells. Eur J Cancer: 30A(11): 1675-82.

Pain VM. (1996) Initiation of protein synthesis in eukaryotic cells. Eur J Biochem; 236(3): 747-71.

Parker RA, Pearce BC, et al. (1993) Tocotrienols regulate cholesterol production in mammalian cells by post-transcriptional suppression . . . J Biol Chem; 268(15): 11230-8.

Peffley DM, Gayen AK. (1995) "Mevalonate regulates polysome distribution and blocks translation-dependent suppression . . . " Somat Cell Mol Genet; 21(3): 189-204.

Peffley DM, Gayen AK. (1997) "Inhibition of squalene synthese but not squalene cyclase prevents mevalonate-mediated . . . " Arch Biochem Biophys; 337(2): 251-60.

Pollard M. Luckert PH. (1997) Influence of isoflavones in soy protein isolates on development of induced prostate-related cancers in L-W rats. Nutr Cancer; 28(1): 41-5.

Qureshi AA, Burger WC, et al. (1986) The structure of an inhibitor of cholesterol biosynthesis isolated from barley. J Biol Chem; 261(23): 10544-50.

Ravid T, Doolman R, Avner R, et al. (2000) "The ubiquitin-proteasome pathway mediates the regulated degradation of mammalian . . . " J Biol Chem; 275(46): 35840-7.

Reddy KB, Krueger JS, et al. (1999) "Mitogen-activated protein kinase (MAPK) regulates the expression of progelatinase B (MMP-9) in breast . . . " Int J Cancer; 82(2): 268-73.

Rousseau D, Kaspar R, et al. (1996) "Translation initiation of ornithine decarboxylase and nucleocytoplasmic transport of cyclin . . . " Proc Natl Acad Sci U S A; 93(3): 1065-70.

Sakai J, Duncan EA, et al. (1996) "Sterol-regulated release of SREBP-2 from cell membranes requires two sequential cleavages, one within . . . " Cell; 85(7): 1037-46.

Schimmoller F. Simon I, Pfeffer Sr. (1998) Rab GTPases, directors of vesicle docking. J Biol Chem; 273(35): 22161-4.

Shen JC, Klein Rd, et al. (2000) Low-dose genistein induces cyclin-dependent kinase inhibitors and G(1) cell-cycle arrest in human prostate . . . Mol Carcinog; 29(2): 92-102.

Singh RP, Dhawan P, et al. (1999) "One-way cross-talk between p38(MAPK) and p42/44(MAPK). Inhibition of p38 (MAPK) induces low density . . . " J Biol Chem; 274(28): 19593-600.

Sonenberg N. (1994) mRNA translation: influence of the 5' and 3' untranslated regions. Curr Opin Genet Dev; 4(2): 310-5.

Spinozzi F, Pagliacci MC, et al (1994) "The natural tyrosine kinase inhibitor genistein produces cell cycle arrest and apoptosis in Jurkat . . . " Leuk Res; 18(6): 431-9.

Swinnen JV, Heemers H, et al. (2000) "Stimulation of tumor-associated fatty acid synthase expression by growth factor activation of the sterol . . . " Oncogene; 19(45): 5173-81.

Swinnen JV, Ulrix W et al. (1997) "Coordinate regulation of lipogenic gene expression by androgens: evidence for a cascade . . . " Proc Natl Acad Sci U S A; 94(24): 12975-80.

Taraboletti G, D'Ascenzo S, et al. (2002) "Shedding of the matrix metalloproteinases MMP-2, MMP-9, and MT1-MMP . . . " Am J Pathol; 160(2): 673-80.

Vadlamudi RK, Wang RA, et al. (2000) "Evidence of Rab3A expression, regulation of vesicle trafficking, and cellular secretion in response . . . " Mol Cell Biol; 20(23): 9092-101.

Vallett SM, Sanchez HB. et al. (1996) "A direct role for sterol regulatory element binding protein in activation of 3-hydroxy . . . " J Biol Chem; 271(21): 12247-53.

Wang X, Sato R, et al. (1994) SREBP-1, a membrane-bound transcription factor released by sterol-regulated proteolysis. Cell; 77(1): 53-62.

Weber E, Berta G, Tousson A, et al. (1994) Expression and polarized targeting of a rab3 isoform in epithelial cells. J Cell Biol; 125(3): 583-94.

Yao J. Xiong S, et al. (2001) "Multiple signaling pathways involved in activation of matrix metalloproteinase-9 (MMP-9) by herregulin-beta1 in . . . " Oncogene; 20(56): 8066-74.

Yeh S, Lin HK, et al. (1999) "From HER2/Neu signal cascade to androgen receptor and its coactivators: a novel pathway . . . " Proc Natl Acad Sci U S A; 96(10): 5458-63.

Yu L, Hui-Chen F, et al. (1999) Differential expression of RAB5A in human lung adenocarcinoma cells with different metastasis potential. Clin Exp Metastasis; 17(3): 213-9.

Zerial M, McBride H. (2001) Rab proteins as membrane organizers. Nat Rev Mol Cell Biol; 2(2): 107-17.

Zhou Jr, Gugger Et, et al. (1999) Soybean phytochemicals inhibit the growth of transplantable human prostate carcinoma and tumor angiogenesis in mice. J Nutr; 129(9): 1628-3.

U.S. Appl. No. 60/362,358, filed Mar. 7, 2002, Elson et al.
U.S. Appl. No. 60/364,288, filed Mar. 14, 2002, Mo et al.
U.S. Appl. No. 60/374,307, filed Apr. 19, 2002, Mo et al.

* cited by examiner

COMPOSITION AND METHOD FOR TREATING CANCER

CROSS-REFERENCE TO RELATED APPLICATIONS

This application claims priority from U.S. provisional patent application No 60/362,358 filed Mar. 7, 2002, which is incorporated by reference as if fully set forth herein. This application also incorporates by reference all of the subject matter disclosed in U.S. provisional patent applications No. 60/364,288, filed Mar. 14, 2002, and No. 60/374,307, filed April 19, 2002, as if fully set forth herein.

STATEMENT REGARDING FEDERALLY SPONSORED RESEARCH OR DEVELOPMENT

This invention was made with U.S. government support awarded by the United States National Institutes of Health Grant Nos.: CA72527 entitled "Dietary Isoprenoid Regulation of Growth Related Genes" funded through the National Cancer Institute; CA81756 entitled "Modulation of Mevalonate Synthesis by Dietary Isoprenoids" funded through the National Cancer Institute; and CA73418 entitled "Cancer Prevention by Iosprenoid Constituents of Plants" funded through the National Cancer Institute. The United States has certain rights to this invention.

FIELD OF THE INVENTION

The present invention relates to a composition and an associated method of using the composition for impeding growth of cancer cells by subjecting cancer cells to a composition containing an effective amount of a synergistic mixture of at least a pair of HMG-CoA reductase inhibitors.

BACKGROUND

Prostate cancer is the most common non-skin malignancy in men, second only to lung cancer for cancer-related male deaths in the United States. There is a high prevalence of latent or occult prostate cancer in U.S. males over 50 years old. That is, post mortem studies have estimated that approximately 30 percent of males older than age 50 have histologic evidence of prostate cancer, in which it is even reported that some U.S. males, as early as 20 years of age, have detectable precursor lesions. Therefore, it is not surprising that the presence of microscopic adenocarcinoma foci in 30 to 50 year old U.S. males has been estimated to range from 25 to 32 percent. Yet, prostate cancer is relatively uncommon in male populations in many Asian countries.

Epidemiological studies have suggested that dietary intake of fruits and vegetables and other plant-related products may provide significant chemopreventive effects against hormone-related cancers. A number of micronutrients, in particular, β-carotene, ascorbic acid, α-tocopherol and folic acid, have been intensely studied to elucidate any corresponding chemopreventive effects that these micronutrients may convey when consumed. However, many of the results of these micronutrient studies have led to contradictory or inconclusive findings concerning their chemopreventive effectiveness.

A growing body of evidence indicates that anutrients, hereinafter defined as non-nutrient phytochemicals, such as anti-oxidants, dithiothriones, phenols, indoles, flavonoids, protease inhibitors and allium compounds, may also play key roles in either blocking or suppressing carcinogenic processes. Even though it is now generally considered that a wide variety of anutrients in plant-related diets is a primary contributor to chemoprevention, it is generally believed that a single anutrient compound is unlikely to be the sole cause of chemoprevention from these plant-related diets. Rather it appears that it is likely that multiple anutrient components impinge on multiple key cell growth signaling pathways simultaneously as the primary prevention mechanism of any cancer attributable to anutrients.

More recently, a subcategory of phytochemical anutrients, i.e., the secondary products of plant mevalonate metabolism, collectively defined herein as isoprenoids, has been recognized for its potential use in cancer prevention and treatment possibilities. Isoprenoid anutrient compounds are derived entirely or in part from the plant mevalonate biosynthetic pathway, which are further subcategorized into "pure" or "mixed" isoprenoids. Pure isoprenoids have varying structures consisting only of five-carbon isoprene units, e.g., monoterpenes, diterprenes, etc. Some important examples of pure isoprenoids include farnesol, limonene, perillyl alcohol, lycopenes, β-carotenes and ionone. Mixed isoprenoids include isoflavones, prenylated coumarins, flavones, flavanols, chalcones, quinones, and chromanols, each with only a part of the molecule derived via the mevalonate pathway. Some important examples of mixed isoprenoids include the tocotrienols.

Therefore, it is not surprising that a large number of studies have established the anti-tumorigenic properties of pure isoprenoids. It has been clearly shown that isoprenoids, e.g., limonene, perillyl alcohol, γ-tocotrienol, β-ionone, and farnesol, initiate apoptosis and concomitantly arrest cancer cells in the G1 phase of the cell cycle. Tocotrienols have been shown to be especially effective at inhibiting growth of both murine and human breast cancer cells in culture. Pure and mixed isoprenoids have been shown to suppress growth of a vast number of whole animal tumor models including implanted leukemic cells, melanomas, pancreatic tumors and hepatomas.

Since many forms of cancer are considered incurable, in particular prostate cancer, then treatment methods and associated compounds aimed at impeding growth of cancer cell growth are likely to be found useful in aiding in the cure and prevention of these cancers. Therefore, there is a need to identify new and useful compounds and associated methods to treat various cancers for use in impeding cancer cell growth.

SUMMARY OF THE INVENTION

The present compositions and associated methods of treating cancer cells, according to the principles of the present invention, overcome the shortcomings of the prior art by providing a composition including at least a first and a second HMG-CoA reductase inhibitor, wherein the total amount of the first and second HMG-CoA reductase inhibitors is effective in eliciting a synergistic effect on impeding cancer cell growth and wherein the the synergistic effect on impeding cancer cell growth brought about from the total amount of the first and second HMG-CoA reductase inhibitors is greater than a theoretical additive effect from the combined first and second HMG-CoA reductase inhibitors, wherein the composition does not simultaneously contain both a tocotrienol and an ionone when the composition contains only a first and second HMG-CoA reductase inhibitors. The method includes treating cancer cells with the claimed composition to impede cancer cell growth.

By the term "HMG-CoA reductase inhibitor", as used herein, we mean any chemical or compound which is capable of directly or indirectly encumbering a cell's metabolic pathway(s) by interfering with the regulation of the mammalian mevalonate biosynthesis by inhibiting the production of 3-hydroxy-3-methylglutaryl coenzyme A (HMG-CoA) reductase. Thereby any HMG-CoA reductase inhibitor will limit the ability of the cell to produce HMG-CoA reductase. For instance, one would expect an HMG-CoA reductase inhibitor to result in a partial prevention of non-sterol polyisoprenyl compounds, such as farnesyl-pyrophosphate and geranylgeranyl pyrophosphate. A HMG-CoA reductase inhibitor would also be expected to inhibit post-translational incorporation of metabolites of (RS)-[5-3H] mevalonolactone into prenylated proteins. Some important examples of HMG-CoA reductase inhibitors are pure isoprenoids, mixed isoprenoids, flavanoids and statins.

By the terms "treatment", as used herein, we mean slowing the growth of the carcinoma, reducing the mass of the cancer cells, eliminating the cancer cells, preventing cancer cells from being established in a living organism, controlling the growth of the cancer cells, or repressing the cancer cells from transforming into a secondary carcinoma.

By the term "treating", as used herein, we mean exposing the cancer cells to the composition, injecting the composition intravenously, dispensing the composition intraperitoneally, interjecting the composition subcutaneously, administering the composition intramuscularly, applying the composition intrathecally, swallowing the composition orally, inserting the composition rectally, rubbing of the composition topically, and inhaling the composition.

By the term "cell toxicity", as used herein, we mean an adverse chemical effect on normal (noncancerous) cells which is sufficient to cause death of normal cells. By excessive toxicity is meant adverse effects on normal (noncancerous) cells which are sufficient to cause the death of the living organism.

By the term "cancer cells", as used herein, we mean any carcinoma, pre-carcinoma condition, and metastatic carcinoma condition. More preferable, the composition and associated methods of the present invention are intended to be used for the treatment of cancers selected from the group consisting of cancers of the central nervous system, gastrointestinal tract, epidermal system, head and neck system, genitourinary tract, lymphatic system, cardiovascular system, hepatic system and respiratory system.

By the term "isoprenoid", as used herein, we mean a member of a "pure" or a "mixed" isoprenoid. Pure isoprenoids have varying structures consisting only of five-carbon isoprene units, e.g., monoterpenes, diterprenes, etc. Some important examples of pure isoprenoids of the present invention include farnesol, limonene, perillyl alcohol, tocotrienols, ionone and taxol. Some important ionone pure isoprenoids of the present invention are selected from the group consisting of 4-(2,6,6-trimethyl-1-cyclohexen-1-yl)-3-buten-2-one; 4-(2,6,6-trimethyl-2-cyclohexen-1-yl)-3-buten-2-one; 6,10-dimethyl-9,10,-epoxy-undec-3,5-ene-2-one; 9,10-diacetoxy-6,10-dimethyl-undec-3,5-ene-2-one; and 6,10-dimethyl-9,10-diol-undec-3,5-ene-2-one. Some important tocotrienol pure isoprenoids of the present invention are selected from the group consisting of 2,5,7,8-trimethyl-2-(4,8,12-trimethyltrideca-3,7,11-trienyl)-chroman-6-ol; 2,5,8-trimethyl-2-(4,8,12-trimethyltrideca-3,7,11-trienyl)-chroman-6-ol; 2,7,8-trimethyl-2-(4,8,12-trimethyltrideca-3,7,11-trienyl)-chroman-6-ol; and 2,8-dimethyl-2-(4,8,12-trimethyltrideca-3,7,11-trienyl)-chroman-6-ol. Mixed isoprenoids include isoflavones, prenylated coumarins, flavones, flavanols, chalcones, quinones, and chromanols, each with only a part of the molecule derived via the mevalonate pathway. Some important examples of mixed isoprenoids intended for use in the present invention are selected from the group consisting of lycopenes and β-carotenes. Other important HMG-CoA reductase inhibitors from the isoprenoid class of compounds are selected from the group consisting of geranyl tiglate, geranyl antranilate, farnesyl benzoate, farnesyl tiglate, farnesyl anthranilate, geranyl-O-acetylhydroquinone, and farnesyl-O-acetylhydroquinone.

By the term "bioflavonoids", as used herein, we mean any polyphenolic compounds that are ubiquitous in nature and are categorized, according to chemical structure, by having two benzene rings connected by a three carbon chain. The some important classes which are distinguished by the types of molecules found at the different numbered positions are flavonols, isoflavonols, flavones, flavonones, isoflavonones, isoflavones, anthocyandins, chalchones and catechins. Some important isoflavones include genistein, daidzein, and glycitein. Other important HMG-CoA reductase inhibitors from the isoflavones class of compounds are selected from the group consisting of ellagic acid, cathechin, qercetin, equol, epigallocathechin-3-gallate, resverstrol, quercetin and N-acetylcysteine.

By the term "statin", as used herein, we mean fungal metabolite extracts and derivatives (ML-236B/compactin/monocalin K) isolated from *Pythium ultimum, Monacus ruber, Penicillium citrinum, Penicillium brevicompactum* and *Aspergillus terreus*. These statins act as analogs of 3-hydroxy-3-methylglutaric acid (HMG) and are capable of competing with HMG-CoA for the substrate binding site on HMG-CoA reductase. Statins are available by prescription in the U.S., such as, lovastatin (Mevacor/Merck), simvastatin (Zocor/Merck, pravastatin (Pravachol/Bristol-Myers Squibb) and fluvastatin (Lescol/Sandoz). Lovastatin is also known under the chemical structure name of [1S-[1α(R*), 3α,7β,8β(2S*,4S*), 8a.β.]]-2-methylbutanoic acid 1,2,3,7, 8,8a-hexahydro-3,7-dimethyl-8-[2-(tetrahydro-4-hydroxy-6-oxo-2H-pyran-2-yl) ethyl]-1-naphthalenyl ester. Pravastatin also known as pravastin sodium is also known under the chemical structure name of [1S -[1α(βS*,δS*), 2α,6α,8β-(R*), 8aα]]-1,2,6,7,8,8a-hexahydro-β,δ,6-trihydroxy-2-methyl-8-(2-methyl-1-oxobutoxy)-1-naphthalene-heptanoic acid monosodium salt. Simvastatin is also known under the chemical structure name of [1S-[1α,3α,7β,8β, (2S*,4S*), 8aβ]]-2,2-Dimethylbutanoic acid 1,2,3,7,8,8a-hexahydro-3,7-di-methyl-8-[2-tetrahydro-4-hydroxy-6-oxo-2H-pyran-2-yl) -ethyl]-1-naphthalenyl ester. Fluvastatin is also known under the chemical structure name of: [R,S-(E)]-(±)-7-[3(4-fluorophenyl)-1-(1-methyl-ethyl)-1H-indol-2-yl]-3,5-dihydroxy-6-heptenoic acid, monosodium salt.

By the term "synergistic", as used herein, we mean a percentage reduction in cancer cell numbers of at least an additional 5% over the additive sum of individual effects or an increase in host survivability of 5% of the additive sum of individual effects. That is, the combination of the inhibitors is measurably more effective in impeding the growth of the cancer cells when combined together as compared to a predicted additive impedance effect on the growth of the cancer cells based on a theoretical admixture of a substantially equivalent amount of the inhibitors. As a consequence of using multiple compounds in a single composition that elicits a synergistic effect, relative to the individual compounds, an effective therapy may be realized from the composition while simultaneously minimizing any adverse toxic effects brought about by these compounds in the composition.

By the term "effective amount", as used herein, we mean a dosage capable of impeding the cancer cell growth, without subjecting the living organism to adverse chemical effects on normal (noncancerous) cells such as those dosages which are sufficient to cause death of normal cells. In one embodiment the dosage for treating cancer cells in accordance with the present invention will be in the range of about 1 milligram to about fifty grams daily for the composition, in which the first HMG-CoA reductase inhibitor comprises about 5% to about 95% w/w of the composition and the second HMG-CoA reductase inhibitor comprises about 5% to about 95% w/w of the composition. In another embodiment the dosage for treating cancer cells in accordance with the present invention will be in the range of about I milligram to about fifty grams daily for the composition, in which the first HMG-CoA reductase inhibitor comprises about 5% to about 95% w/w of the composition, the second HMG-CoA reductase inhibitor comprises about 5% to about 95% w/w of the composition, and the third HMG-CoA reductase inhibitor comprises about 5% to about 95% w/w of the composition. Exact dosages will depend on the extent to which the compounds are metabolized as well as their bioavailability to the target tissue. Appropriate doses in individual cases can be determined by persons of ordinary skill in the art.

By the term "delivery device", as used herein, we mean any known commercially available vehicle capable of delivering the effective amount of the isoprenoid. These delivery devices may be selected from the group consisting of a tablet, a capsule, a solution, a suspension, an emulsion, a foodstuff, a pharmaceutical preparation, a nutritional supplement, and a dietary additive.

In view of the foregoing disadvantages inherent in the known types of compositions and associated methods for treating cancer cells now present in the prior art, the present invention provides an improved composition of least a first and a second HMG-CoA reductase inhibitor, and a new and improved associated method of using the present composition invention to impede the growth of cancer cells. This composition and associated method invention will be described subsequently in great detail, in which the total amount of the first and second HMG-CoA reductase inhibitors is effective in synergistically impeding the growth of cancer cells is not anticipated, rendered obvious, suggested, or even implied by the prior art, either alone or in any combination thereof. To attain this, the present composition and associated method of impeding the growth of cancer cells essentially comprises a first and a second HMG-CoA reductase inhibitor which is more effective in impeding the growth of the cancer cells than a predicted additive impedance effect on the growth of the cancer cells based on a theoretical admixture of a substantially equivalent amount of the first and second inhibitors.

There has thus been outlined, rather broadly, the more important features of the invention in order that the detailed description thereof that follows may be better understood, and in order that the present contribution of the art may be better appreciated.

Numerous aspects, features and advantages of the present invention will be readily apparent to those of ordinary skill in the art upon reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an aspect of the present invention to provide a new and improved composition containing at least a first and a second HMG-CoA reductase inhibitor for use in impeding the growth of cancer cells which elicits a synergistic effect on impeding cancer cell growth.

It is another aspect of the present invention to provide a method of treating cancer cells by impeding cancer cell growth with a composition containing at least a first and a second HMG-CoA reductase inhibitor which elicits a synergistic effect on impeding cancer cell growth.

An even further aspect of the present invention is to provide new and improved compositions for use in treating cancer cells which has a low cost of manufacture with regard to both materials and labor, and which accordingly is then susceptible to low prices of sale to the consuming public, thereby making such compositions economically available to the buying public.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and description matter in which there is illustrated preferred embodiments of the invention.

DESCRIPTION OF THE INVENTION

In one preferred embodiment, the present invention comprises a composition having a first HMG-CoA reductase inhibitor; and a second HMG-CoA reductase inhibitor, wherein the total amount of the first and second HMG-CoA reductase inhibitors is effective in synergistically impeding cancer cell growth and wherein the cancer cell growth synergistic impedance from the total amount of the first and second HMG-CoA reductase inhibitors is greater than a theoretical additive effect from the combined first and second HMG-CoA reductase inhibitors. Tocotrienol and ionone are explicitly restricted from being present together in this preferred embodiment of the composition when the composition contains only a first and a second HMG-CoA reductase inhibitor.

In another preferred embodiment, the present invention comprises a composition having a a first, second and third HMG-CoA reductase inhibitor, wherein the total amount of said first, second and third HMG-CoA reductase inhibitors is effective in synergistically impeding cancer cell growth and wherein the cancer cell growth synergistic impedance from the total amount of said first, second and third HMG-CoA reductase inhibitors is greater than a theoretical additive effect of combined first, second and third HMG-CoA reductase inhibitors.

In yet another preferred embodiment, the present invention comprises a method of impeding the growth of cancer cells, in which the method comprises the step of treating the cancer cells with a composition containing a first HMG-CoA reductase inhibitor; and a second HMG-CoA reductase inhibitor, wherein the total amount of said first and second HMG-CoA reductase inhibitors is effective in synergistically impeding cancer cell growth and wherein the cancer cell growth synergistic impedance from the total amount of said first and second HMG-CoA reductase inhibitors is greater than a theoretical additive effect of combined first and second HMG-CoA reductase inhibitors, wherein said composition does not simultaneously contain both a tocotrienol and an ionone.

Still yet another preferred embodiment, the present invention comprises a method of impeding the growth of cancer cells by treating the cancer cells with a composition containing a first, second and third HMG-CoA reductase inhibitor, wherein the total amount of said first, second and third HMG-CoA reductase inhibitors is effective in synergistically impeding cancer cell growth and wherein the cancer cell growth synergistic impedance from the total amount of said first, second and third HMG-CoA reductase inhibitors is greater than a theoretical additive effect of combined first, second and third HMG-CoA reductase inhibitors.

B16 melanoma cells were grown in monolayer culture (35×10 mm flasks) in 3 ml RPMI 1640 medium supplemented with 10% fetal bovine serum (FBS) and 80 mg gentamicin/L. The cultures, seeded with $3.3 \times 10^4$ cells/mL, were incubated for 24 h at 37° C. in a humidified atmosphere of 5% $CO_2$. The medium was decanted and replaced with fresh medium containing the test agents. Tocotrienol, perillyl alcohol, and geranyl- or farnesyl-hydroquinone ethers were dissolved in ethanol; and lovastatin and genistein were dissolved in dimethyl sulfoxide, DMSO. The incubations were continued for an additional 48 h. All cultures contained 1 ml/L each of ethanol and DMSO. The medium and detached cells were decanted, the monolayer was washed twice with Hanks' Balanced Salt Solution (HBSS) and then incubated with a trypsin-EDTA solution at 37° C. for 2 min. Trypsin was inactivated by suspending the cells in medium containing 10% FBS. The trypsinized cells were pelleted at 250 xg and resuspended in HBSS. Viable cells, cells that excluded 0.4% trypan blue were counted with a hemocytometer; 24-h cell counts were deducted from final cell counts to provide an estimate of the net increase in cell number. The IC50 value is the concentration of an agent required to suppress the net increase in cell number by 50%.

Measurement of B16 cell proliferation was confirmed by using CellTiter 96, Aqueous One Solution (Promega). Seeding density was determined in the following pilot test. B16 cells were maintained in monolayer culture (96-well tissue culture plate) in 0.1 mL of the medium described above. Cultures, seeded in escalating densities (0-8000 cells/well with a 500-cell interval), were incubated for 72 h at 37° C. in a humidified atmosphere of 5% $CO_2$. At 24 h the medium was decanted from each well and replaced with 0.1 mL fresh medium. The 72-h cell populations were determined by adding 20 µl of CellTiter 96, Aqueous One Solution to each well; the plate was held in dark at 37° C. for 2 h and then read at 490 nm with a SPECTRAmax, 190 multi-plate reader with SOFTmax, PRO version 3.0 (Molecular Devices). Cell survival data were assessed as absorbance versus cell seeding density. The absorbance has a linear correlation with cell seeding density up to 2000 B16 cells/well. The midpoint of cell inoculation density, 1000 cells/well, was chosen for B16 cell proliferation assay. This procedure of determining seeding density also applies to all other cell lines in which the CellTiter 96, Aqueous One Solution was used for proliferation assay. In the proliferation assay, B16cells were incubated in 96-well plates for 24 h. The medium was decanted from each well and replaced with 0.1 mL fresh medium containing the test agents. Incubation continued for an additional 48 h. Cell populations of all wells were determined according to CellTiter 96 procedure as described above. Cell proliferation represents the net absorbance, the difference in absorbance between final and 24-h measurements.

Human DU145 prostate carcinoma cells (HTB-81, ATCC) were grown in Eagle's minimal essential medium (MEM) modified to contain 1.0 mmol sodium pyruvate/L, 0.1 mmol nonessential amino acids/L, and 1.5 g sodium bicarbonate/L, supplemented with 10% FBS and 80 mg gentamicin/L. Cultures, seeded in 0.1 mL medium with 1000 cells/well in a 96-well plate, were incubated for 24 h at 37° C. in a humidified atmosphere of 5% $CO_2$. At 24 h the medium was decanted from each well and replaced with 0.1 mL fresh medium containing the test agents. Incubation continued for additional 72 h. Cell populations of all wells were determined using the CellTiter 96 procedure.

Human LNCaP prostate carcinoma cells (CRL-1740, ATCC) were grown in RPMI 1640 medium modified by ATCC to contain 10 mmol/L HEPES, 1 mmol sodium pyruvate/L, 4.5 g glucose/L, 1.5 g sodium bicarbonate/L, supplemented with 10% FBS and 80 mg gentamicin/L. Cultures, seeded in 0.1 mL medium with 2000 cells/well in a 96-well plate, were incubated for 24 h at 37° C. in a humidified atmosphere of 5% $CO_2$. At 24 h the medium was decanted from each well and replaced with 0.1 mL fresh medium containing the test agents. Incubation continued for additional 72 h. Cell populations of all wells were determined using the CellTiter 96 procedure.

Human PC-3 prostate adenocarcinoma cells (CRL-1435, ATCC) were grown in Kaighn's modification of Ham's F12 medium modified to contain 1.5 g sodium bicarbonate/L, supplemented with 10% FBS and 80 mg gentamicin/L. Cultures, seeded in 0.1 mL medium with 1500 cells/well in a 96-well plate, were incubated for 24 h at 37° C. in a humidified atmosphere of 5% $CO_2$. At 24 h the medium was decanted from each well and replaced with 0.1 mL fresh medium containing the test agents. Incubation continued for additional 72 h. Cell populations of all wells were determined using the CellTiter 96 procedure.

Photomicrographs of representative fields of monolayers of cells were made with a microscope equipped with a digital camera coupled with an image-acquisition software package.

EXAMPLE 1

Suppression data of prostate cancer cell growth in cell cultures by exposure to increasing concentrations of genistein are summarized in Table 1. A duplicate exposure study of 0 to 40 μmol/L of genistein was found to suppress the proliferation of DU145 cells with an estimated IC50 of 30 μmol/L. A multiple repeat study of exposure of 0 to 40 μmol/L of genistein was found to suppress the proliferation of PC-3 cells with an estimated IC50 of 70±17 μmol/L.

TABLE 1

Effects of Genistein on Human Prostate Cell Growth.

| Cell Line | Genistein | Absorbance* |
|---|---|---|
| DU145 | 0 μM | 0.56 |
| DU145 | 10 μM | 0.53 |
| DU145 | 20 μM | 0.34 |
| DU145 | 40 μM | 0.20 |
| PC-3 | 0 μM | 0.44 |
| PC-3 | 10 μM | 0.43 |
| PC-3 | 20 μM | 0.39 |
| PC-3 | 40 μM | 0.32 |

*Net Absorbance at 490 nm represents amount of net growth after 72 h.

EXAMPLE 2

Suppression data of prostate cancer cell growth in cell cultures by exposure to increasing concentrations of γ-tocotrienol alone are summarized in Table 2. A triplicate exposure study of 0 to 40 μmol/L of γ-tocotrienol was found to suppress the proliferation of DU145 cells with an estimated IC50 of 20±2 μmol/L. A duplicate study of exposure of 0 to 80 μmol/L of γ-tocotrienol was found to suppress the proliferation of PC-3 cells with an estimated IC50 of 39 μmol/L.

TABLE 2

Effects of γ-Tocotrienol on Human Prostate Cell Growth.

| Cell Line | γ-Tocotrienol | Absorbance* |
|---|---|---|
| DU145 | 0 μM | 0.43 |
| DU145 | 5 μM | 0.39 |
| DU145 | 10 μM | 0.40 |
| DU145 | 20 μM | 0.33 |
| DU145 | 30 μM | 0.20 |
| DU145 | 40 μM | −0.05 |
| PC-3 | 0 μM | 0.43 |
| PC-3 | 40 μM | 0.36 |
| PC-3 | 80 μM | 0.02 |

*Net Absorbance at 490 nm represents amount of net growth after 72 h. A negative number indicates cell killing.

EXAMPLE 3

Suppression of prostate cancer cell growth in cell cultures by exposure to increasing concentrations of perillyl alcohol alone was studied and summarized in Table 3. A duplicate exposure study of 0 to 1600 μmol/L of perillyl alcohol was found to suppress the proliferation of DU145 cells with an estimated IC50 of 420 μmol/L. A duplicate study of exposure of 0 to 800 μmol/L of perillyl alcohol was found to suppress the proliferation of PC-3 cells with an estimated IC50 of 480 μmol/L.

TABLE 3

Effects of Perillyl Alcohol on Human Prostate Cell Growth.

| Cell Line | Perillyl Alcohol | Absorbance* |
|---|---|---|
| DU145 | 0 μM | 0.54 |
| DU145 | 100 μM | 0.46 |
| DU145 | 200 μM | 0.40 |
| DU145 | 400 μM | 0.18 |
| DU145 | 800 μM | −0.06 |
| DU145 | 1600 μM | −0.05 |
| PC-3 | 0 μM | 0.34 |
| PC-3 | 200 μM | 0.34 |
| PC-3 | 400 μM | 0.09 |
| PC-3 | 600 μM | 0.06 |
| PC-3 | 800 μM | −0.05 |

*Net Absorbance at 490 nm represents amount of net growth after 72 h. A negative number indicates cell killing.

EXAMPLE 4

Suppression data of prostate cancer cell growth in culture by exposure to increasing concentrations of lovastatin alone are summarized in Table 4. A triplicate exposure study of 0 to 32 μmol/L of lovastatin was found to suppress the proliferation of DU 145 cells with an estimated IC50 of 18±2 μmol/L. A quadruplicate study of exposure of 0 to 4 μmol/L of lovastatin was found to suppress the proliferation of PC-3 cells with an estimated IC50 of 2.2±0.5 μmol/L

TABLE 4

Effects of Lovastatin on Human Prostate Cell Growth.

| Cell Line | Lovastatin | Absorbance* |
|---|---|---|
| DU145 | 0 μM | 0.36 |
| DU145 | 4 μM | 0.37 |
| DU145 | 8 μM | 0.30 |
| DU145 | 16 μM | 0.18 |
| DU145 | 32 μM | 0.15 |
| PC-3 | 0 μM | 0.43 |
| PC-3 | 1 μM | 0.32 |
| PC-3 | 2 μM | 0.10 |
| PC-3 | 4 μM | −0.02 |

*Net Absorbance at 490 nm represents amount of net growth after 72 h. A negative number indicates cell killing.

EXAMPLE 5

Growth suppression of prostate cancer cell cultures exposed to genistein and γ-tocotrienol, separately and in combination, is summarized in Table 5. Simultaneous exposure of genistein and γ-tocotrienol to prostate cancer cell cultures was found to elicit a synergistic effect on impeding the growth of the cancer cells.

TABLE 5

Effects of Genistein and Tocotrienol on Prostate Cancer Cells in Culture.

| Cell Line | Genistein | γ-Tocotrienol | Growth* | Conclusion |
|---|---|---|---|---|
| PC3 | 20 μM | — | 87% | — |
| PC3 | — | 20 μM | 100% | — |
| PC3 | 20 μM | 20 μM | 3% | Synergistic |
| PC3 | 40 μM | — | 78% | — |
| PC3 | 40 μM | 20 μM | 2% | Synergistic |
| DU145 | 10 μM | — | 100% | — |
| DU145 | — | 5 μM | 87% | — |

TABLE 5-continued

Effects of Genistein and Tocotrienol on Prostate Cancer Cells in Culture.

| Cell Line | Genistein | γ-Tocotrienol | Growth* | Conclusion |
|---|---|---|---|---|
| DU145 | 10 μM | 5 μM | 94% | — |
| DU145 | 20 μM | — | 97% | — |
| DU145 | — | 10 μM | 68% | — |
| DU145 | 20 μM | 10 μM | 29% | Synergistic |
| DU145 | — | 20 μM | 70% | — |
| DU145 | 20 μM | 20 μM | 30% | Synergistic |
| LNCaP | 10 μM | — | 100% | — |
| LNCaP | — | 5 μM | 100% | — |
| LNCaP | 10 μM | 5 μM | 80% | Synergistic |
| LNCaP | 20 μM | — | 70% | — |
| LNCaP | — | 20 μM | 70% | — |
| LNCaP | 20 μM | 20 μM | 30% | Synergistic |

*Average percent cell survival after exposure period relative to the control group.

EXAMPLE 6

Growth suppression of melanoma cancer cell cultures exposed to genistein and tocotrienol, separately and in combination, is summarized in Table 6. Simultaneous exposure of genistein and γ-tocotrienol to melanoma cancer cell cultures was found to elicit a synergistic effect on impeding the growth of the cancer cells.

TABLE 6

Effects of Genistein and Tocotrienol on Melanoma Cells in Culture.

| Cell Line | Genistein | γ-Tocotrienol | Growth* | Conclusion |
|---|---|---|---|---|
| B16 | 2.5 μM | — | 100% | — |
| B16 | — | 2.5 μM | 100% | — |
| B16 | 2.5 μM | 2.5 μM | 96% | — |
| B16 | 5 μM | — | 83% | — |
| B16 | — | 5 μM | 73% | — |
| B16 | 5 μM | 5 μM | 41% | Synergistic |

*Average percent cell survival after exposure period relative to the control group

EXAMPLE 7

Growth suppression of prostate cancer cell cultures exposed to genistein and farnesol, separately and in combination, is summarized in Table 7. Simultaneous exposure of genistein and farnesol to prostate cancer cell cultures was found to elicit a synergistic effect on impeding the growth of the cancer cells.

TABLE 7

Effects of Genistein and Farnesol on Human Prostate Cell Growth in Culture.

| Cell Line | Genistein | Farnesol | Growth* | Conclusion |
|---|---|---|---|---|
| PC3 | 10 μM | — | 121 ± 3% | — |
| PC3 | — | 50 μM | 53 ± 5% | — |
| PC3 | 10 μM | 50 μM | 12 ± 3% | Synergistic |
| PC3 | 40 μM | — | 74 ± 11% | — |
| PC3 | — | 100 μM | 93 ± 7% | — |
| PC3 | 40 μM | 100 μM | 53 ± 4% | Synergistic |
| DU145 | 10 μM | — | 93% | — |
| DU145 | — | 50 μM | 38% | — |
| DU145 | 10 μM | 50 μM | 17% | Synergistic |
| DU145 | 40 μM | — | 38 ± 10% | — |
| DU145 | — | 100 μM | 79 ± 11% | — |
| DU145 | 40 μM | 100 μM | 5 ± 20% | Synergistic |

*Average percent cell survival after exposure period relative to the control group.

EXAMPLE 8

Suppression data of melanoma cancer cell cultures exposed to genistein and farnesol, separately and in combination, are summarized in Table 8. The simultaneous exposure of genistein and farnesol to melanoma cancer cell cultures was found to elicit a synergistic effect on impeding the growth of the cancer cells.

TABLE 8

Effects of Genistein and Farnesol on Melanoma Cells in Culture.

| Cell Line | Farnesol | Genistein | Predicted Growth* | Observed Growth** | Conclusion |
|---|---|---|---|---|---|
| B16 | 12.5 μM | — | — | 84% | — |
| B16 | 25 μM | — | — | 54% | — |
| B16 | — | 2.5 μM | — | 84% | — |
| B16 | — | 5.0 μM | — | 63% | — |
| B16 | 12.5 μM | 2.5 μM | 68 ± 17% | 57 ± 13% | Synergistic |
| B16 | 12.5 μM | 5.0 μM | 48 ± 23% | 37 ± 6% | Synergistic |
| B16 | 25 μM | 2.5 μM | 38 ± 15% | 29 ± 15% | Synergistic |
| B16 | 25 μM | 5.0 μM | 24 ± 13% | 13 ± 9% | Synergistic |

*Predicted percentage survival rates of the cancer cell population calculated from arithmetically combining the separate toxicities of each phytochemical corresponding to their respective experimental dosages.
**Empirical percentage survival rates measured from simultaneous exposure of both phytochemicals during 40 hour exposure.

EXAMPLE 9

Suppression of prostate cancer cell cultures exposed to genistein and taxol, separately and in combination, is summarized in Table 9. Simultaneous exposure of genistein and taxol was found to elicit a synergistic effect on impeding the growth of the cancer cells.

TABLE 9

Effects of Genistein and Taxol on Human Prostate Cell Growth in Culture.*

| Cell Line | Genistein | Taxol | Growth* | Conclusion |
|---|---|---|---|---|
| PC3 | 20 μM | — | 95 ± 4% | — |
| PC3 | — | 2 nM | 97 ± 5% | — |
| PC3 | 20 μM | 2 nM | 95 ± 4% | — |
| PC3 | — | 5 nM | 71 ± 1% | — |
| PC3 | 20 μM | 5 nM | 69 ± 3% | — |
| PC3 | 40 μM | — | 84 ± 2% | — |
| PC3 | 40 μM | 2 nM | 74 ± 5% | Synergistic |

*Average percent cell survival after exposure period relative to the control group.

EXAMPLE 10

Suppression data of prostate cancer cell cultures exposed to genistein and lovastatin, separately and in combination, are summarized in Table 10. Simultaneous exposure of genistein and lovastatin was found to elicit a synergistic effect on impeding the growth of the cancer cells.

TABLE 10

Effects of Genistein and Lovastatin on Human Prostate Cell Growth in Culture.

| Cell Line | Genistein | Lovastatin | Growth* | Conclusion |
|---|---|---|---|---|
| PC3 | 20 μM | — | 95 ± 4% | — |
| PC3 | — | 0.75 μM | 87 ± 3% | — |
| PC3 | 20 μM | 0.75 μM | 78 ± 8% | Synergistic |
| PC3 | — | 1.5 μM | 57 ± 4% | — |
| PC3 | 20 μM | 1.5 μM | 33 ± 13% | Synergistic |
| PC3 | 40 μM | — | 84 ± 2% | — |
| PC3 | 40 μM | 0.75 μM | 62 ± 2% | Synergistic |
| PC3 | 40 μM | 1.5 μM | 25 ± 2% | Synergistic |

*Average percent cell survival after exposure period relative to the control group.

EXAMPLE 11

Suppression data of prostate cancer cell cultures exposed to tocotrienol and lovastatin, separately and in combination, are summarized in Table 11. Simultaneous exposure of tocotrienol and lovastatin was found to elicit a synergistic effect on impeding the growth of the cancer cells.

TABLE 11

Effects of Tocotrienol and Lovastatin on Human Prostate Cell Growth in Culture.

| Cell Line | Lovastatin | γ-Tocotrienol | Growth* | Conclusion |
|---|---|---|---|---|
| DU145 | 1.5 μM | — | 100% | — |
| DU145 | — | 5 μM | 87% | — |
| DU145 | 1.5 μM | 5 μM | 90% | — |
| DU145 | 3.0 μM | — | 100% | — |
| DU145 | — | 10 μM | 68% | — |
| DU145 | 3.0 μM | 10 μM | 19% | Synergistic |

TABLE 11-continued

Effects of Tocotrienol and Lovastatin on Human Prostate Cell Growth in Culture.

| Cell Line | Lovastatin | γ-Tocotrienol | Growth* | Conclusion |
|---|---|---|---|---|
| LNCaP | 1.5 μM | — | 100% | — |
| LNCaP | — | 5 μM | 100% | — |
| LNCaP | 1.5 μM | 5 μM | 100% | Synergistic |
| LNCaP | 3.0 μM | — | 100% | — |
| LNCaP | — | 10 μM | 76% | — |
| LNCaP | 3.0 μM | 10 μM | 28% | Synergistic |

*Average percent cell survival after exposure period relative to the control group.

EXAMPLE 12

Suppression data of melanoma cancer cell cultures exposed to tocotrienol and lovastatin, separately and in combination, are summarized in Table 12. Simultaneous exposure of tocotrienol and lovastatin was found to elicit a synergistic effect on impeding the growth of the cancer cells.

TABLE 12

Effects of Tocotrienol and Lovastatin on Melanoma Tumor Cells in Culture.

| Cell Line | Lovastatin | γ-Tocotrienol | Growth* | Conclusion |
|---|---|---|---|---|
| B16 | 0.5 μM | — | 100% | — |
| B16 | — | 2.5 μM | 100% | — |
| B16 | 0.5 μM | 5 μM | 30% | Synergistic |
| B16 | 1.0 μM | — | 83% | — |
| B16 | — | 5 μM | 73% | — |
| B16 | 1.0 μM | 5 μM | 5% | Synergistic |

*Average percent cell survival after exposure period relative to the control group.

EXAMPLE 13

Suppression data of melanoma cancer cell cultures exposed to lovastatin and farnesyl tiglate, separately and in combination, are summarized in Table 13. Simultaneous exposure of tocotrienol and lovastatin was found to elicit a synergistic effect on impeding the growth of the cancer cells.

TABLE 13

Effects of Lovastatin and Farnesyl Tiglate on Melanoma Tumor Cells in Culture.

| Cell Line | Lovastatin | Farsenyl Tiglate | Growth* | Conclusion |
|---|---|---|---|---|
| B16 | 1.5 μM | — | 73% | — |
| B16 | — | 25 μM | 70% | — |
| B16 | 1.5 μM | 25 μM | 54% | — |
| B16 | — | 50 μM | 49% | — |
| B16 | 1.5 μM | 50 μM | 43% | — |
| B16 | 3.0 μM | — | 42% | — |
| B16 | 3.0 μM | 25 μM | 20% | Synergistic |
| B16 | 3.0 μM | 50 μM | 4% | Synergistic |

*Average percent cell survival after exposure period relative to the control group.

EXAMPLE 14

Growth suppression of prostate cancer cell cultures exposed to genistein, lovastatin and γ-tocotrienol, separately and in combination, is summarized in Table 14. Simultaneous exposure of genistein, lovastatin and γ-tocotrienol to prostate cancer cell cultures was found to elicit a synergistic effect on impeding the growth of the cancer cells.

squares fits of the frequency emission spectra. Simultaneous exposure of genistein, lovastatin and γ-tocotrienol to prostate cancer cell cultures was found to induce an increase in G1 phase cells and a decrease in S phase cells. Simultaneous exposure of genistein, lovastatin and γ-tocotrienol to prostate cancer cell cultures was also found to elicit a synergistic effect on impeding the growth of the cancer cells.

TABLE 14

Effects of Genistein, Lovastatin and Tocotrienol on Human Prostate Cell Growth in Culture.

| Cell Line | Genistein | Lovastatin | γ-Tocotrienol | Growth* | Conclusion |
|---|---|---|---|---|---|
| LNCaP | 10 μM | — | — | 100% | — |
| LNCaP | — | 1.5 μM | — | 100% | — |
| LNCaP | — | — | 5 μM | 100% | — |
| LNCaP | 10 μM | 1.5 μM | — | 100% | — |
| LNCaP | 10 μM | — | 5 μM | 80% | Bi-Synergistic |
| LNCaP | — | 1.5 μM | 5 μM | 100% | — |
| LNCaP | 10 μM | 1.5 μM | 5 μM | 61% | Tri-Synergistic |
| LNCaP | 20 μM | — | — | 99% | — |
| LNCaP | — | 3 μM | — | 100% | — |
| LNCaP | — | — | 10 μM | 76% | — |
| LNCaP | 20 μM | 3 μM | — | 97% | — |
| LNCaP | 20 μM | — | 10 μM | 74% | — |
| LNCaP | — | 3 μM | 10 μM | 28% | Bi-Synergistic |
| LNCaP | 20 μM | 3 μM | 10 μM | 4% | Tri-Synergistic |
| DU145 | 10 μM | — | — | 100% | — |
| DU145 | — | 1.5 μM | — | 100% | — |
| DU145 | — | — | 5 μM | 87% | — |
| DU145 | 10 μM | 1.5 μM | — | 100% | — |
| DU145 | 10 μM | — | 5 μM | 94% | — |
| DU145 | — | 1.5 μM | 5 μM | 90% | — |
| DU145 | 10 μM | 1.5 μM | 5 μM | 57% | Tri-Synergistic |
| DU145 | 20 μM | — | — | 97% | — |
| DU145 | — | 3 μM | — | 100% | — |
| DU145 | — | — | 10 μM | 68% | — |
| DU145 | 20 μM | 3 μM | — | 100% | — |
| DU145 | 20 μM | — | 10 μM | 29% | Bi-Synergistic |
| DU145 | — | 3 μM | 10 μM | 19% | Bi-Synergistic |
| DU145 | 20 μM | 3 μM | 10 μM | 0% | Tri-Synergistic |

*Average percent cell survival after exposure period relative to the control group.

EXAMPLE 15

Growth suppression of prostate cancer cell cultures exposed to genistein, lovastatin and γ-tocotrienol, separately and in combination, is summarized in Table 15 which depicts cell phase distribution profiles associated with DU145 cancer cell cultures exposed to these HMG-CoA reductase inhibitors. Subsequent to the treatment of the cancer cells with these HGM-CoA reductase inhibitors, the cells were fixed in ethanol, treated with RNase and stained with propidium iodine. Fluorescent measurements were then made via a flow cytometer using a laser. A double discriminator was used as the primary gate to eliminate cell aggregates. The distribution profiles associated with the various phases (G1, S) were then obtained through the use of least

TABLE 15

Effects of Genistein, Lovastatin and Tocotrienol on Human Prostate Cell Growth in Culture.

| Cell Type | Control | Genistein (10 μM) | Lovastatin (1.5 μM) | γ-Tocotrienol (5 μM) | Composite Mixture* |
|---|---|---|---|---|---|
| G1 | 65.4% | 64.9% | 62.0% | 66.7% | 72.1% |
| S | 23.0% | 19.3% | 22.3% | 21.1% | 17.2% |
| G2 | 11.6% | 15.8% | 15.7% | 12.2% | 10.7% |
| Growth** | 100% | 100% | 100% | 87% | 57% |

*Genistein at 10 μM, Lovastatin at 1.5 μM and γ-Tocotrienol at 5 μM..
**Average percent cell survival relative to the control group after 72 h exposure period.

EXAMPLE 16

Growth suppression of melanoma cancer cell cultures exposed to genistein, lovastatin and geranyl anthranilate, separately and in combination, is summarized in Table 16 which depicts cell phase distribution profiles associated with B16 cancer cell cultures exposed to these HMG-CoA reductase inhibitors. Subsequent to the treatment of the cancer cells with these HGM-CoA reductase inhibitors, the cells were fixed in ethanol, treated with RNase and stained with propidium iodine. Fluorescent measurements were then made via a flow cytometer using a laser. A double discriminator was used as the primary gate to eliminate cell aggregates. The distribution profiles associated with the various phases (G1, S) were then obtained through the use of least squares fits of the frequency emission spectra. Simultaneous exposure of genistein, lovastatin and geranyl anthranilate to melanoma cancer cell cultures was found to induce an increase in G1 phase cells and a decrease in S phase cells.

TABLE 16

Effects of Genistein, Lovastatin and Geranyl Anthranilate on Melanoma Cell Growth in Culture.

| Cell Type | Control | Genistein (5 μM) | Lovastatin (0.5 μM) | Geranyl Anthranilate (30 μM) | Composite Mixture* |
|---|---|---|---|---|---|
| G1 | 64.9% | 67.6% | 68.5% | 67.3% | 75.6% |
| S | 22.5% | 21.7% | 22.2% | 22.9% | 14.0% |
| G2 | 12.7% | 10.8% | 9.3% | 9.8% | 10.5% |
| Growth** | 100% | 73% | 71% | 81% | 47% |

*Genistein at 5 μM, Lovastatin at 0.5 μM and geranyl anthranilate at 30 μM..
**Average percent cell survival relative to the control group after 72 h exposure period.

As to the manner of usage and operation of the present invention, the same should be apparent from the above description. Accordingly, no further discussion relating to the manner of usage and operation will be provided.

While preferred embodiments of the method and associated kit for treating cancer have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A composition for use in impeding the growth of cancer cells, said composition comprising: a first HMG-CoA reductase inhibitor comprising tocotrienol; a second HMG-CoA reductase inhibitor comprising genistein; and a third HMG-CoA reductase inhibitor comprising lovastatin, wherein the total amount of said first, second and third HMG-CoA reductase inhibitors is effective in synergistically impeding cancer cell growth and wherein the cancer cell growth synergistic impedance from the total amount of said first, second and third HMG-CoA reductase inhibitors is greater than a theoretical additive effect of combined first, second and third HMG-CoA reductase inhibitors wherein the cancer cells are selected from the group consisting of cancer tumors of the central nervous system, gastrointestinal tract, epidermal system, head and neck system, genitourinary tract, lymphatic system, cardiovascular system, hepatic system and respiratory system and wherein the impedance of cancer cell growth is selected from a treatment group consisting of slowing the growth of the cancer cells, reducing the mass of the cancer cells, controlling the growth of the cancer cells, and repressing the cancer cells from transforming into a secondary carcinoma.

2. The composition of claim 1 wherein said composition is in a delivery device selected from the group consisting of a tablet, a capsule, a solution, a suspension, an emulsion, a foodstuff, a pharmaceutical composition, a dietary supplement composition, and a nutritional supplement composition.

3. The composition of claim 1 wherein said first HMG-CoA reductase inhibitor comprises an amount of 5% w/w to 95% w/w of said composition; said second HMG-CoA reductase inhibitor comprises an amount of 5% w/w to 95% w/w of said composition; and said third HMG-CoA reductase inhibitor comprises an amount of 5% w/w to 95% w/w of said composition.

4. The composition of claim 1 wherein said first HMG-CoA reductase inhibitor comprises an amount of 5 μg/daily dosage to 10 g/daily dosage of said composition; said second HMG-CoA reductase inhibitor comprises an amount of 5 μg/daily dosage to 10 g/daily dosage of said composition; and said third HMG-CoA reductase inhibitor comprises an amount of 5 μg/daily dosage to 10 g/daily dosage of said composition.

5. A method of impeding the growth of cancer cells, said method comprising the step of treating the cancer cells with a composition containing a first HMG-CoA reductase inhibitor comprising tocotrienol; a second HMG-CoA reductase inhibitor comprising genistein; and a third HMG-CoA reductase inhibitor comprising lovastatin, wherein the total amount of said first, second and third HMG-CoA reductase inhibitors is effective in synergistically impeding cancer cell growth and wherein the cancer cell growth synergistic impedance from the total amount of said first, second and third HMG-CoA reductase inhibitors is greater than a theoretical additive effect of combined first, second and third HMG-CoA reductase inhibitors, wherein the cancer cells are selected from the group consisting of cancer tumors of the central nervous system, gastrointestinal tract, epidermal system, head and neck system, genitourinary tract, lymphatic system, cardiovascular system, hepatic system and respiratory system and wherein the impedance of cancer cell growth is selected from a treatment group consisting of slowing the growth of the cancer cells, reducing the mass of the cancer cells, controlling the growth of the cancer cells, and repressing the cancer cells from transforming into a secondary carcinoma.

6. The method of claim 5 wherein said treating step is selected from the group consisting of exposing the cancer cells to the composition, injecting the composition intravenously, dispensing the composition intraperitoneally, interjecting the composition subcutaneously, administering the composition intramuscularly, applying the composition intrathecally, swallowing the composition orally, inserting the composition rectally, rubbing of the composition topically, and inhaling the composition.

7. The method of claim 5 wherein the treating step results in impeding the growth of the cancer cells by inducing an increase in G1 phase cells and a decrease in S phase cells.

* * * * *